US011439393B2

(12) United States Patent
Shelton, IV et al.

(10) Patent No.: US 11,439,393 B2
(45) Date of Patent: *Sep. 13, 2022

(54) SLIP RING ASSEMBLY FOR SURGICAL INSTRUMENT

(71) Applicant: Cilag GmbH International, Zug (CH)

(72) Inventors: Frederick E. Shelton, IV, Hillsboro, OH (US); Jason L. Harris, Lebanon, OH (US); David C. Yates, West Chester, OH (US); Chester O. Baxter, III, Loveland, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 155 days.

This patent is subject to a terminal disclaimer.

(21) Appl. No.: 16/836,256

(22) Filed: Mar. 31, 2020

(65) Prior Publication Data

US 2020/0275929 A1 Sep. 3, 2020

Related U.S. Application Data

(63) Continuation of application No. 15/934,190, filed on Mar. 23, 2018, now Pat. No. 10,631,861.

(51) Int. Cl.
*A61B 17/072* (2006.01)
*A61B 17/32* (2006.01)
(Continued)

(52) U.S. Cl.
CPC .......... *A61B 17/07207* (2013.01); *A61B 17/320092* (2013.01); *A61B 17/068* (2013.01);
(Continued)

(58) Field of Classification Search
CPC ............ A61B 17/068; A61B 17/072; A61B 17/07207; A61B 17/115; A61B 17/1155;
(Continued)

(56) References Cited

U.S. PATENT DOCUMENTS 5,391,166 A 2/1995 Eggers
5,699,406 A 12/1997 Liikanen et al.
(Continued)

FOREIGN PATENT DOCUMENTS

EP 2839797 A2 2/2015
WO WO 2015/153642 A1 10/2015

OTHER PUBLICATIONS

Hollister, S., "Waterproofing explained: How Apple, Samsung and Sony keep the liquid out," clnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.

*Primary Examiner* — Scott A Smith
(74) *Attorney, Agent, or Firm* — Frost Brown Todd LLC

(57) ABSTRACT

A surgical instrument includes a body assembly, a shaft assembly extending distally from the body assembly along a shaft axis, and an end effector at a distal end of the shaft assembly. The shaft assembly includes an outer tube configured to rotate relative to the body assembly about the shaft axis. The surgical instrument further includes a slip ring assembly configured to enable electrical communication between the shaft assembly and the body assembly while permitting relative rotation therebetween. The slip ring assembly includes a first electrical contact supported by the outer tube, and a second electrical contact electrically coupled with the first electrical contact and positioned radially outward of the outer tube. The first electrical contact is configured to rotate with the outer tube about the shaft axis relative to the second electrical contact while the first and second electrical contacts remain electrically coupled.

20 Claims, 14 Drawing Sheets

(51) Int. Cl.
*H01R 35/02* (2006.01)
*A61B 17/068* (2006.01)
*A61B 17/29* (2006.01)
*A61B 17/00* (2006.01)

(52) U.S. Cl.
CPC ... *A61B 17/072* (2013.01); *A61B 2017/00398* (2013.01); *A61B 2017/07214* (2013.01); *A61B 2017/2927* (2013.01); *A61B 2017/320097* (2017.08); *H01R 35/02* (2013.01)

(58) Field of Classification Search
CPC .......... A61B 2017/07214; A61B 2017/00017; A61B 2017/00398; A61B 2017/00473; A61B 2017/00734; A61B 2017/07285; A61B 2017/2927; A61B 90/90; A61B 90/98
USPC .. 227/19, 175.1, 176.1, 175.2, 178.1, 180.1; 606/1, 139, 153, 213, 219
See application file for complete search history.

(56) References Cited

U.S. PATENT DOCUMENTS

| | | |
|---|---|---|
| 5,792,135 A | 8/1998 | Madhani et al. |
| 5,817,084 A | 10/1998 | Jensen |
| 5,817,093 A | 10/1998 | Williamson, IV et al. |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,404,508 B2 | 7/2008 | Smith et al. |
| 7,524,320 B2 | 4/2009 | Tierney et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 7,887,530 B2 | 2/2011 | Zemlok et al. |
| 8,408,439 B2 | 4/2013 | Huang et al. |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,608,045 B2 | 12/2013 | Smith et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,991,678 B2 | 3/2015 | Wellman et al. |
| 9,072,535 B2 | 7/2015 | Shelton, IV et al. |
| 9,186,142 B2 | 11/2015 | Fanelli et al. |
| 9,301,759 B2 | 4/2016 | Spivey et al. |
| 9,345,481 B2 | 5/2016 | Hall et al. |
| 9,724,094 B2 | 8/2017 | Baber et al. |
| 9,795,379 B2 | 10/2017 | Leimbach et al. |
| 9,839,425 B2 | 12/2017 | Zergiebel et al. |
| 9,913,642 B2 | 3/2018 | Leimbach et al. |
| 10,631,860 B2 | 4/2020 | Bakos et al. |
| 10,631,861 B2 | 4/2020 | Shelton, IV et al. |
| 10,639,037 B2 | 5/2020 | Shelton, IV et al. |
| 10,639,038 B2 | 5/2020 | Scott et al. |
| 10,765,427 B2 | 9/2020 | Shelton, IV et al. |
| 10,779,828 B2 | 9/2020 | Shelton, IV et al. |
| 10,799,257 B2 | 10/2020 | Worthington et al. |
| 10,842,517 B2 | 11/2020 | Posey et al. |
| 2007/0221497 A1 | 9/2007 | Egawa et al. |
| 2009/0090763 A1 | 4/2009 | Zemlok et al. |
| 2011/0192884 A1 | 8/2011 | Whitman et al. |
| 2012/0071866 A1 | 3/2012 | Kerr et al. |
| 2013/0131650 A1 | 5/2013 | Whitman et al. |
| 2014/0263541 A1 | 9/2014 | Leimbach et al. |
| 2014/0263552 A1 | 9/2014 | Hall et al. |
| 2015/0108201 A1 | 4/2015 | Williams |
| 2015/0316431 A1 | 11/2015 | Collins et al. |
| 2015/0351765 A1 | 12/2015 | Valentine et al. |
| 2016/0066911 A1 | 3/2016 | Baber et al. |
| 2016/0265938 A1 | 9/2016 | Hryb et al. |
| 2016/0310134 A1 | 10/2016 | Contini et al. |
| 2019/0000472 A1 | 1/2019 | Shelton, IV et al. |
| 2019/0000478 A1 | 1/2019 | Messerly et al. |
| 2019/0290269 A1 | 9/2019 | Shelton, IV et al. |
| 2019/0290273 A1* | 9/2019 | Shelton, IV ..... A61B 17/07207 |
| 2020/0275929 A1* | 9/2020 | Shelton, IV ........... H01R 39/12 |

* cited by examiner

SLIP RING ASSEMBLY FOR SURGICAL INSTRUMENT

This application is a continuation of U.S. patent application Ser. No. 15/934,190, entitled "Slip Ring Assembly for Surgical Instrument," filed Mar. 23, 2018, and issued as U.S. Pat. No. 10,631,861 on Apr. 28, 2020, the disclosure of which is incorporated by reference herein.

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
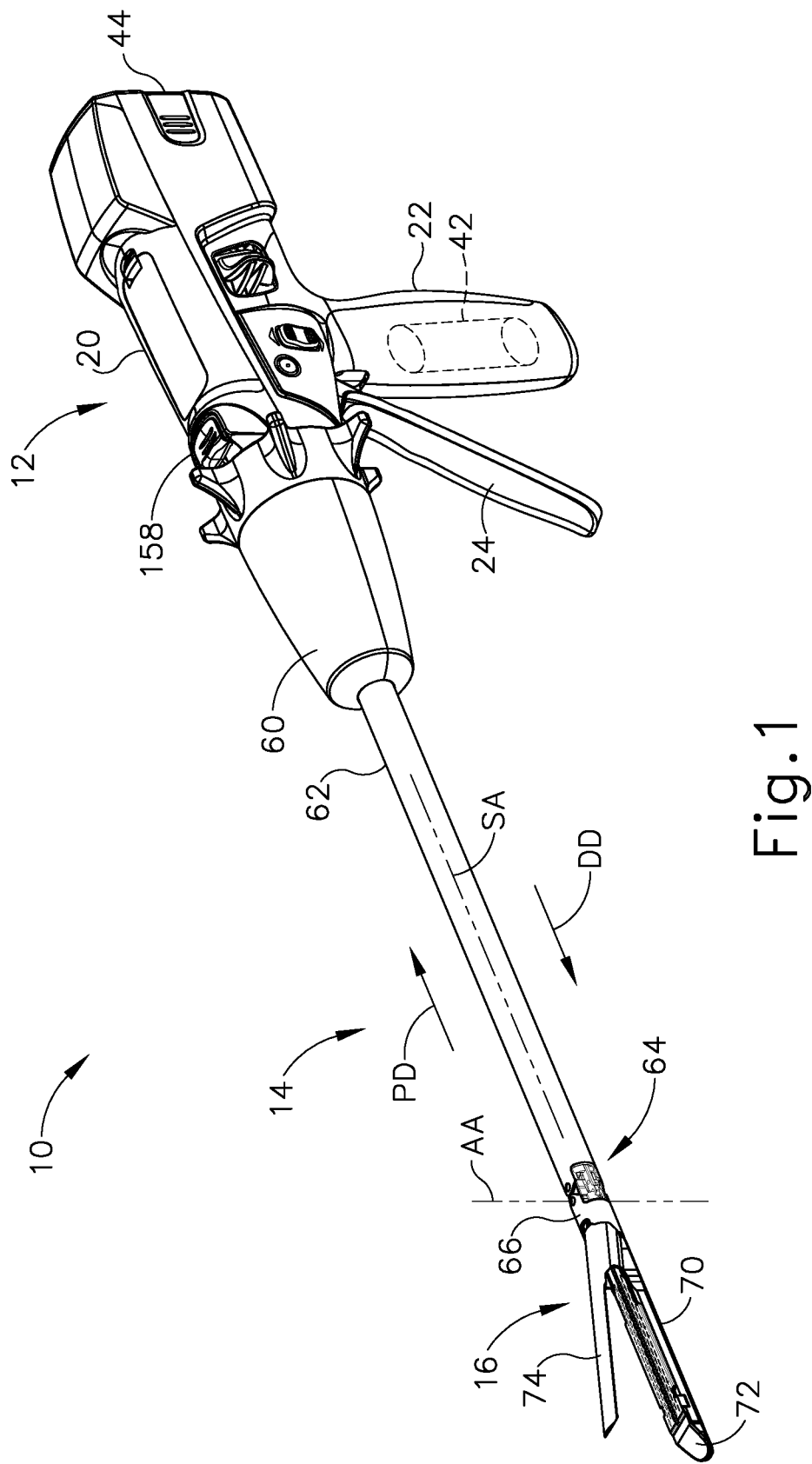
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Surgical Stapling Instrument

Figure 2:
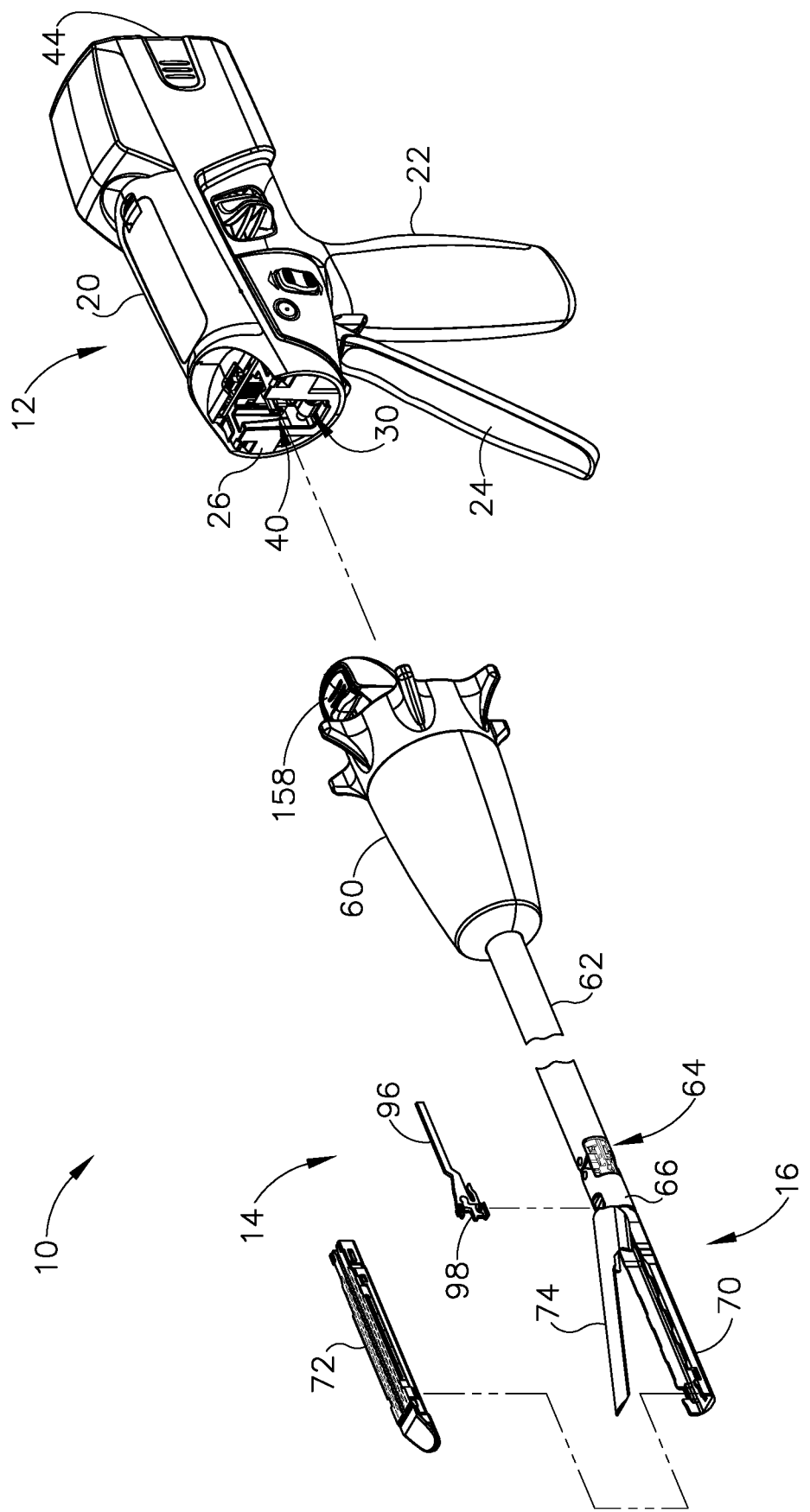
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
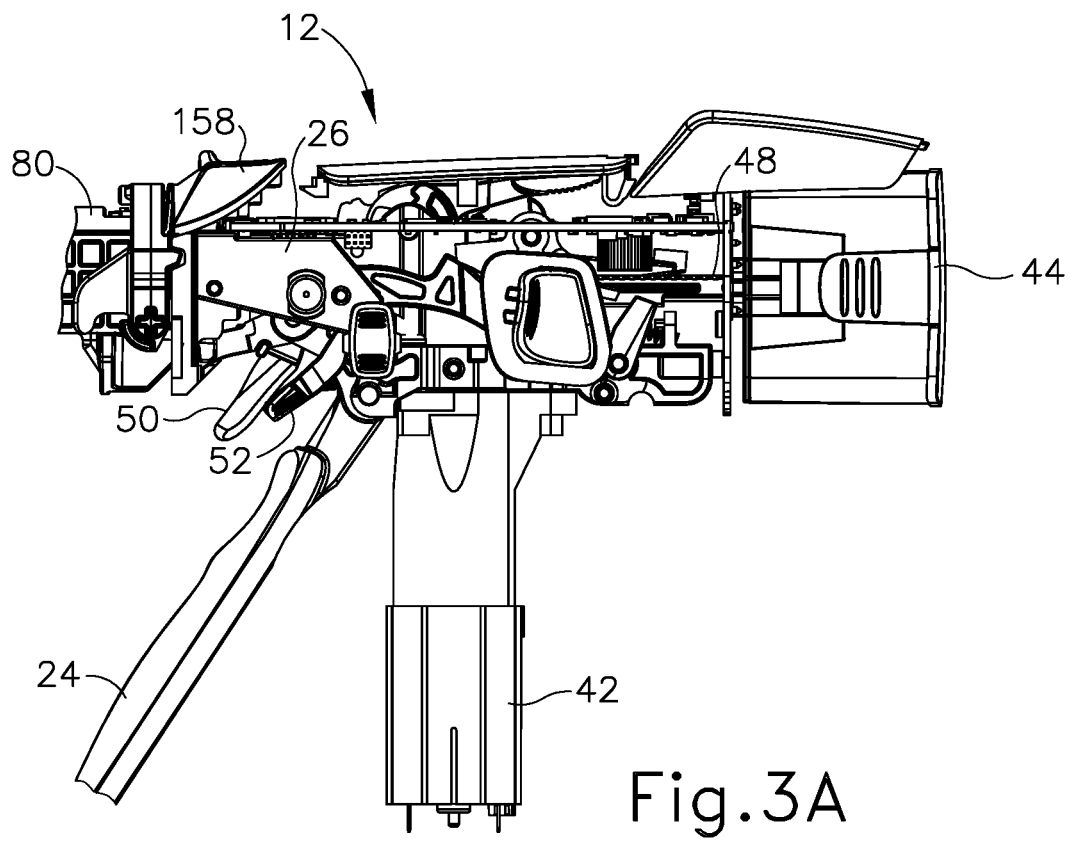
FIG. 3A depicts a side elevational view of the surgical instrument of FIG. 1, with a body of the handle assembly omitted, showing a closure trigger of the handle assembly in an unactuated position.
Figure 3B:
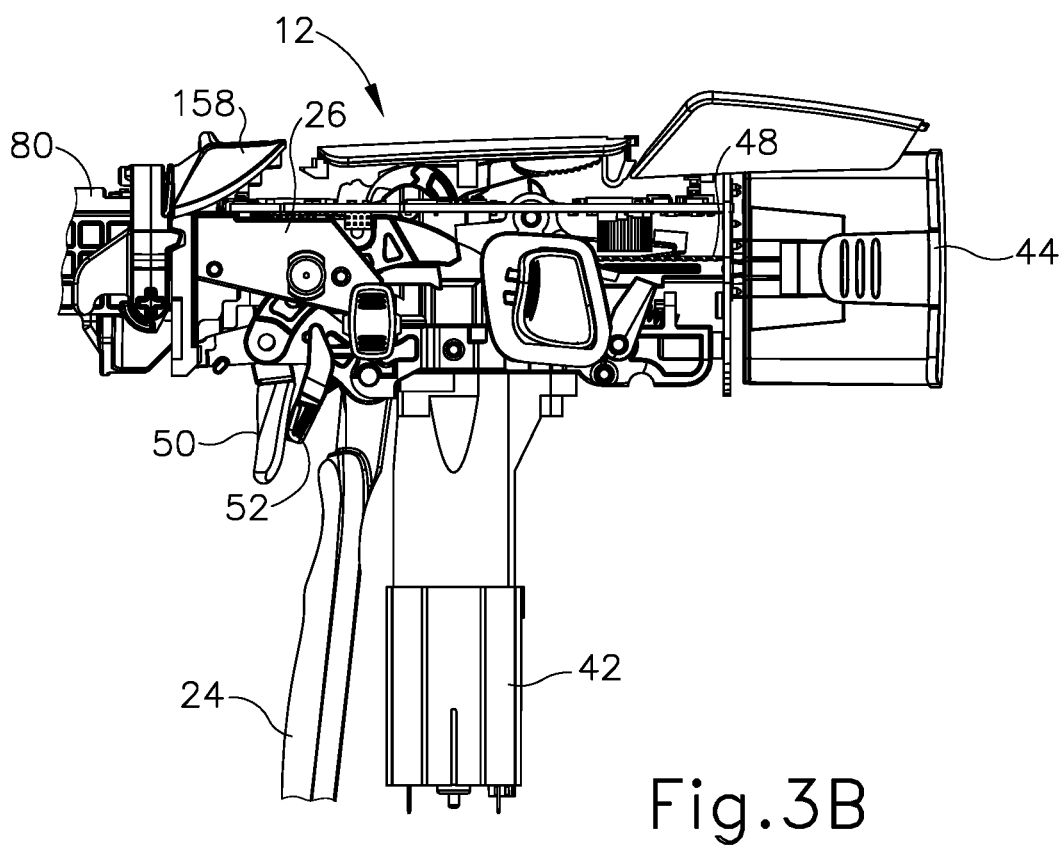
FIG. 3B depicts a side elevational view of the surgical instrument of FIG. 1, with a body of the handle assembly omitted, showing a closure trigger of the handle assembly in an actuated position.
Figure 4:
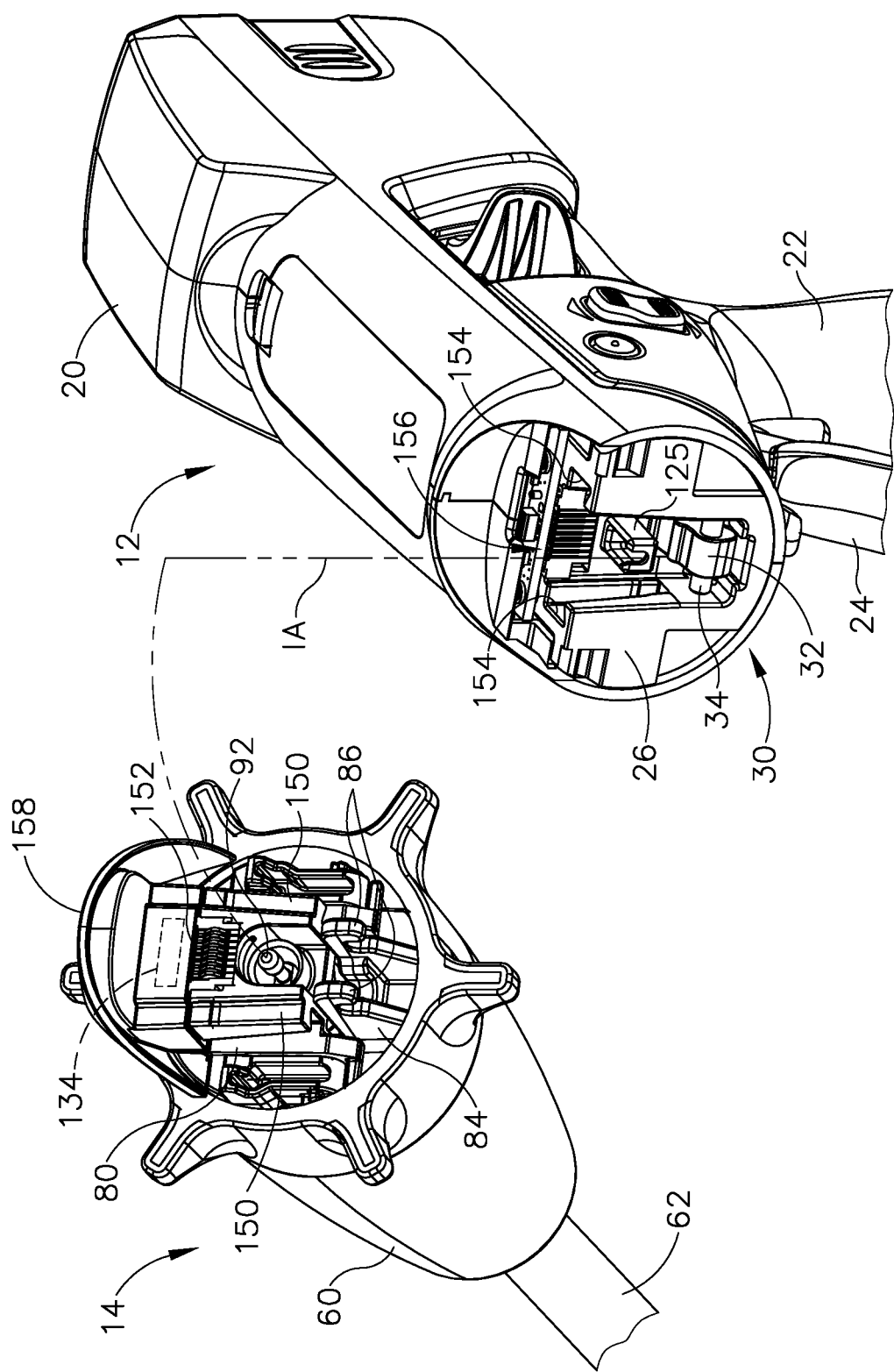
FIG. 4 depicts another perspective view of the surgical instrument of FIG. 1 in a separated state, showing additional details of a distal end of the handle assembly and a mating proximal end of the interchangeable shaft assembly.

As seen in FIGS. 2-4, handle assembly body (20) houses a support structure in the form of a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12)

and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
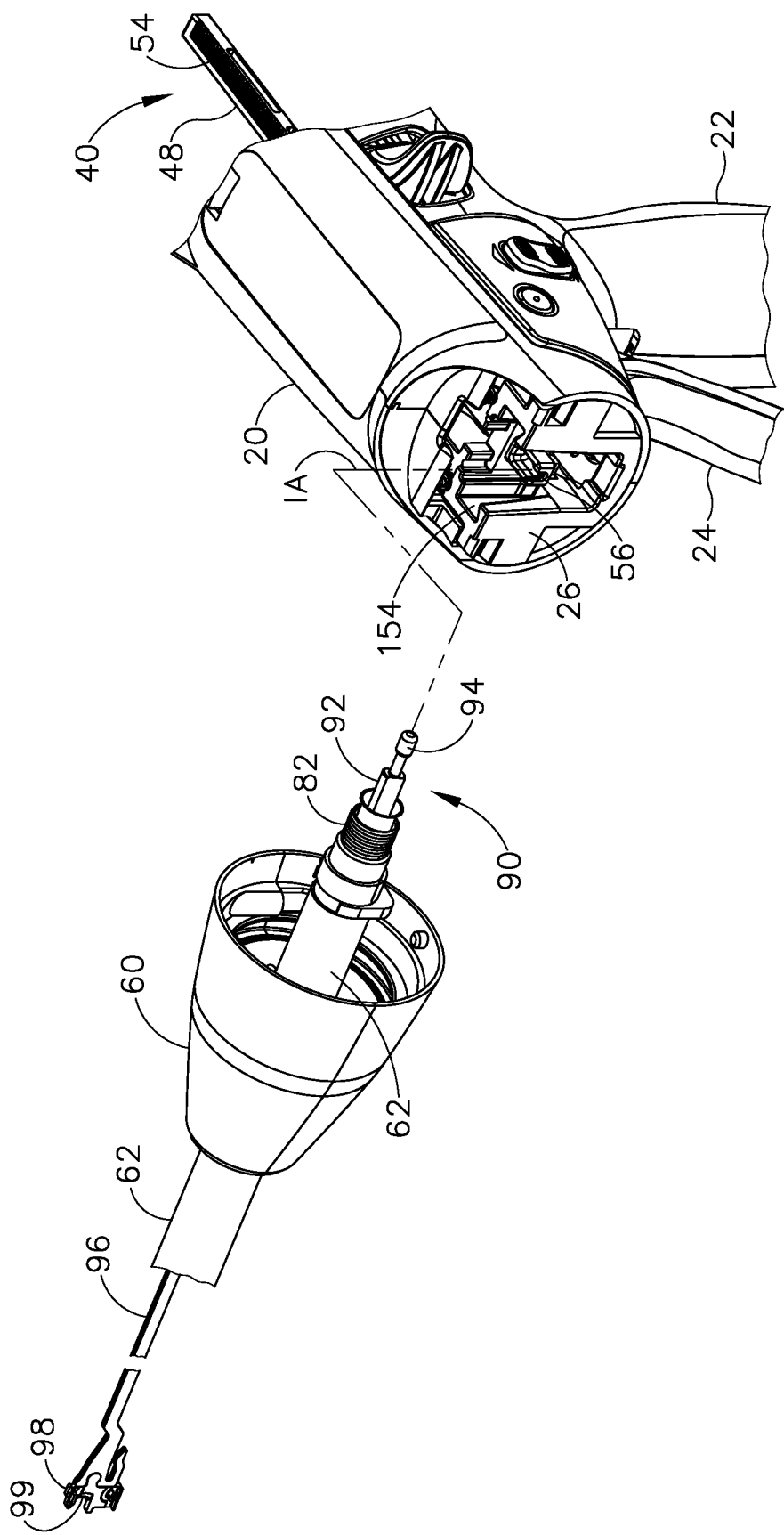
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to configured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. Ser. No. 15/636,096, entitled "Surgical System Couplable With Staple Cartridge And Radio Frequency Cartridge, And Method Of Using Same," filed Jun. 28, 2017, published as U.S. Pub. No. 2019/0000478 on Jan. 3, 2019, issued as U.S. Pat. No. 11,298,128 on Apr. 12, 2022, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a support structure in the form of a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
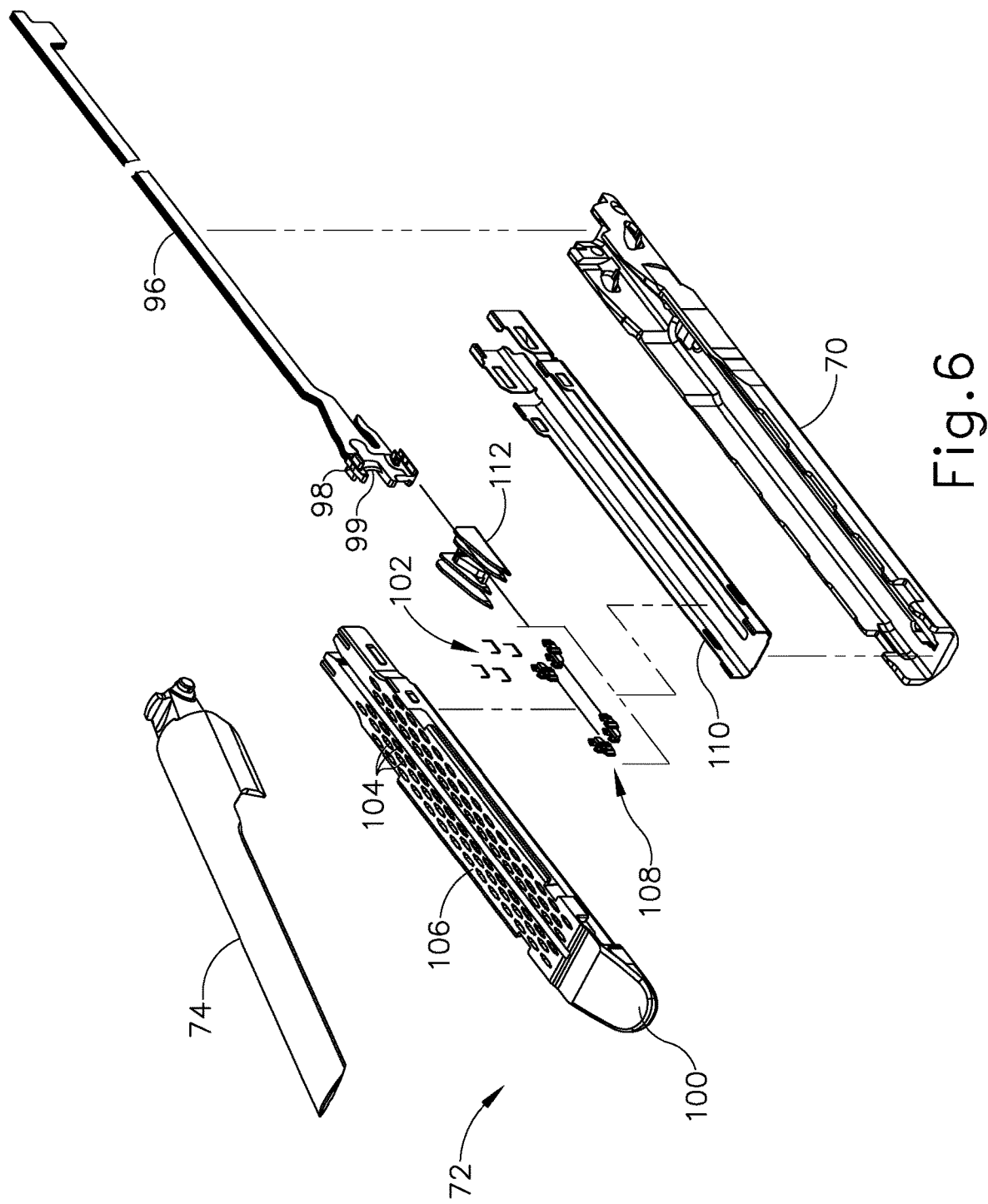
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections Within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one or more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
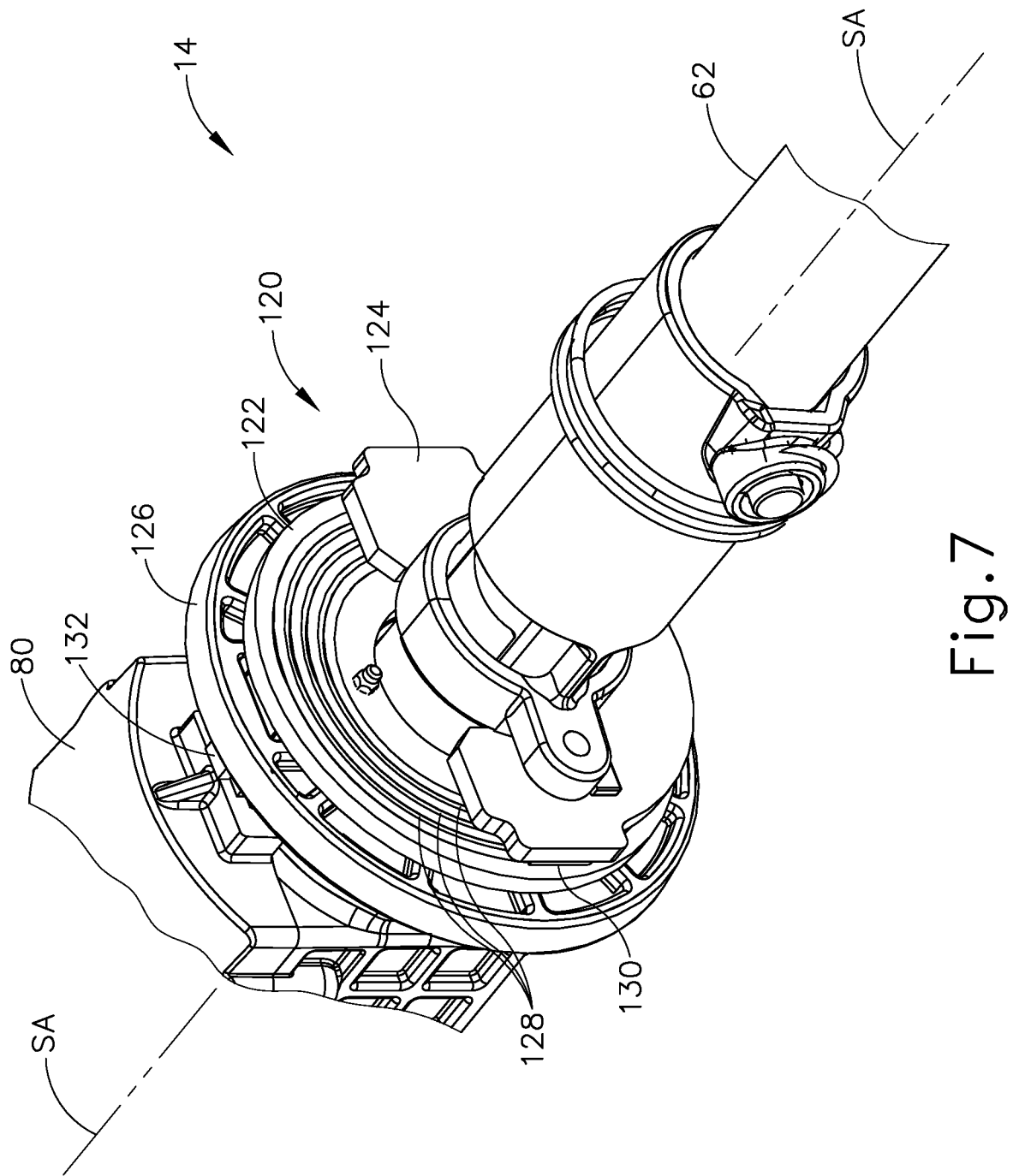
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) includes a slip ring assembly (120) housed within nozzle (60). Slip ring assembly (120) is configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122), about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156) arranged therebetween. Handle electrical connector (156) is in electrical communication with handle circuit board (46) of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156). The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. Ser. No. 15/635,663, entitled "Method For Articulating A Surgical Instrument," filed Jun. 28, 2017, published as U.S. Pub. No. 2019/0000465 on Jan. 3, 2019, issued as U.S. Pat. No. 10,765,427 on Sep. 8, 2020; U.S. Ser. No. 15/635,631, entitled "Surgical Instrument With Axially Movable Closure Member," filed Jun. 28, 2017, published as U.S. Pub. No. 2019/0000464 on Jan. 3, 2019, issued as U.S. Pat. No. 10,639,037 on May 5, 2022; U.S. Ser. No. 15/635,837, entitled "Surgical Instrument Comprising An Articulation System Lockable To A Frame," filed Jun. 28, 2017, published as U.S. Pub. No. 2019/0000472 on Jan. 3, 2019, issued as U.S. Pat. No. 11,246,592 on Feb. 15, 2022; U.S. Pat. Pub. No. 2016/0066911, entitled "Smart Cartridge Wake Up Operation And Data Retention," published Mar. 10, 2016, issued as U.S. Pat. No. 10,135,242 on Nov. 20, 2018; U.S. Pat. Pub. No. 2015/0272575, entitled "Surgical Instrument Comprising A Sensor System," published Oct. 1, 2015, issued as U.S. Pat. No. 9,913,642 on Mar. 13, 2018; U.S. Pat. Pub. No. 2014/0263552, entitled "Staple Cartridge Tissue Thickness Sensor System," published Sep. 18, 2014 now abandoned; and/or U.S. Pat. Pub. No. 2014/0263541, entitled "Articulatable Surgical Instrument Comprising An Articulation Lock," published Sep. 18, 2014, now abandoned, the disclosures of which are incorporated by reference herein.

E. Exemplary End Effector With Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
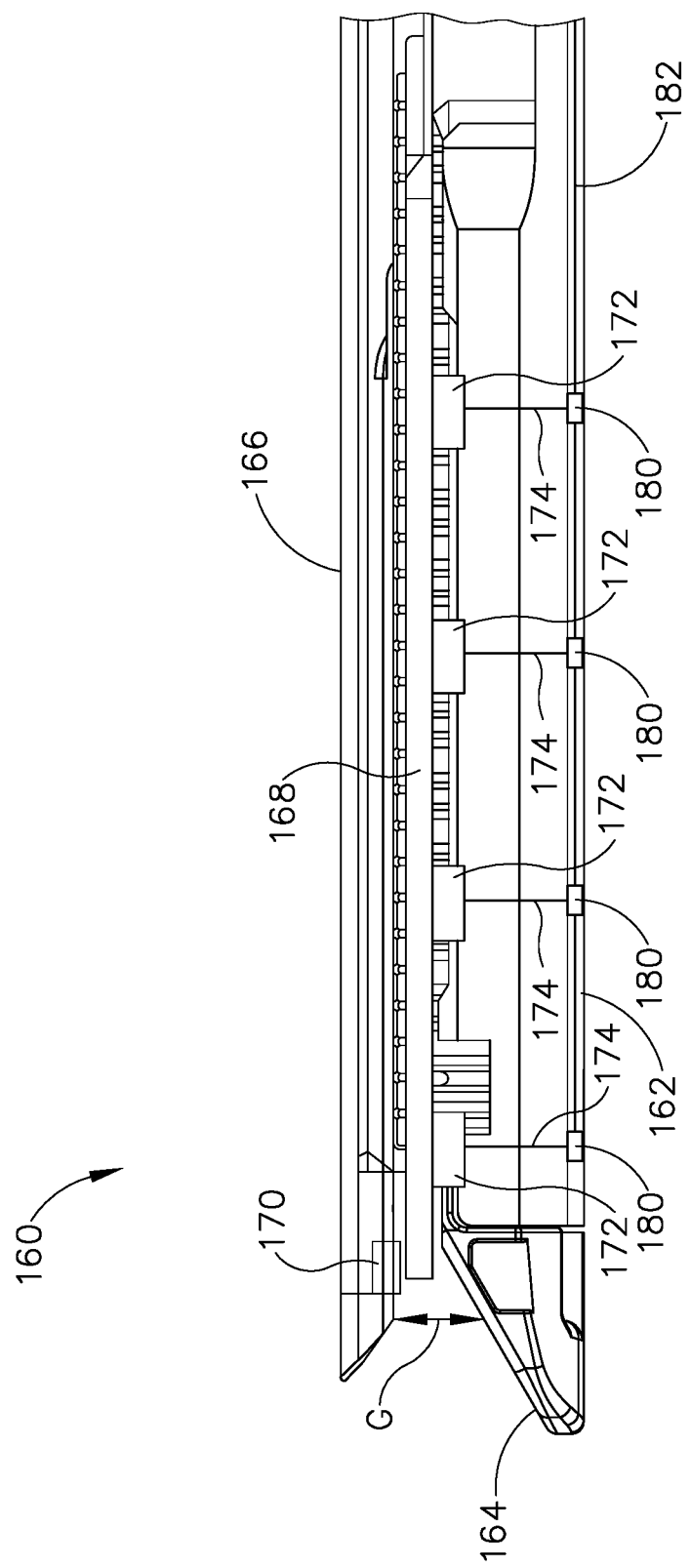
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of channel (162). In other versions, one or more sensors, such as one or more of second sensors (172), may be provided on staple cartridge (164). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, in versions in which second sensors (172) are provided on staple cartridge (164), second sensors (172) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130) of slip ring assembly (120). Therefore, when staple cartridge (164) is suitably coupled with channel (162), second sensors (172) are in electrical communication with shaft circuit board (134).

II. Exemplary Slip Ring Assembly with Axially Spaced Electrical Contacts

During use of surgical instrument (10) in surgical procedures, certain electrical components of instrument (10) may be vulnerable to fluid ingress, which can undesirably cause shorting of corresponding electrical pathways in instrument (10). For instance, a conductive fluid bridge could form between two or more of annular electrical contacts (128) of slip ring assembly (120), allowing an electrical short circuit to occur through the fluid bridge. Such electrical short circuiting could result in the failure of one or more electrical systems of surgical instrument (10). The exemplary slip ring assembly (200) described below includes various features that are configured to prevent electrical shorting between its electrical contacts in the presence of fluid. Similar to slip ring assembly (120) described above, slip ring assembly (200) is configured to enable electrical communication between shaft assembly (14) and handle assembly (12) while permitting relative rotation therebetween.

Figure 9:
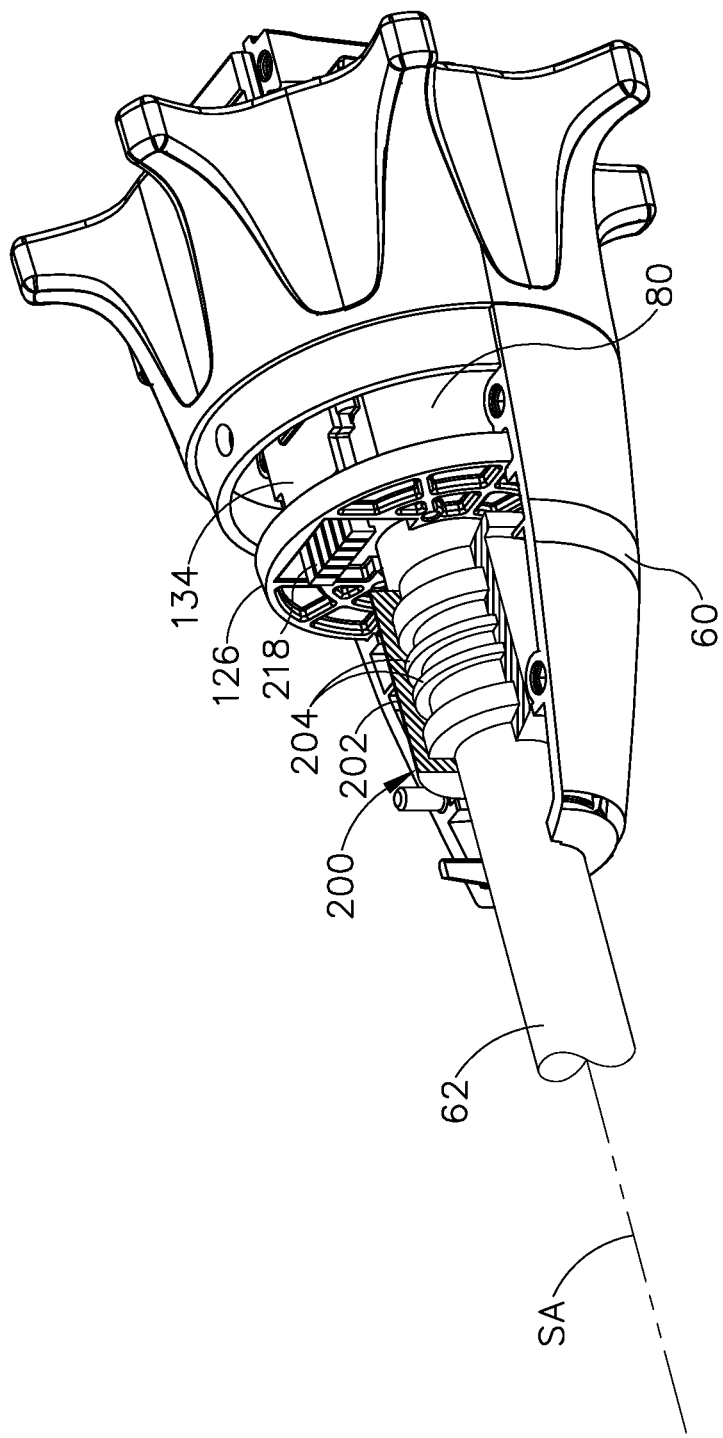
FIG. 9 depicts a perspective view of a proximal portion of the shaft assembly of the surgical instrument of FIG. 1, showing an exemplary alternative slip ring assembly housed within the nozzle, with an upper portion of the nozzle omitted from view and with a sleeve of the slip ring assembly partially sectioned to expose internal features.
Figure 10:
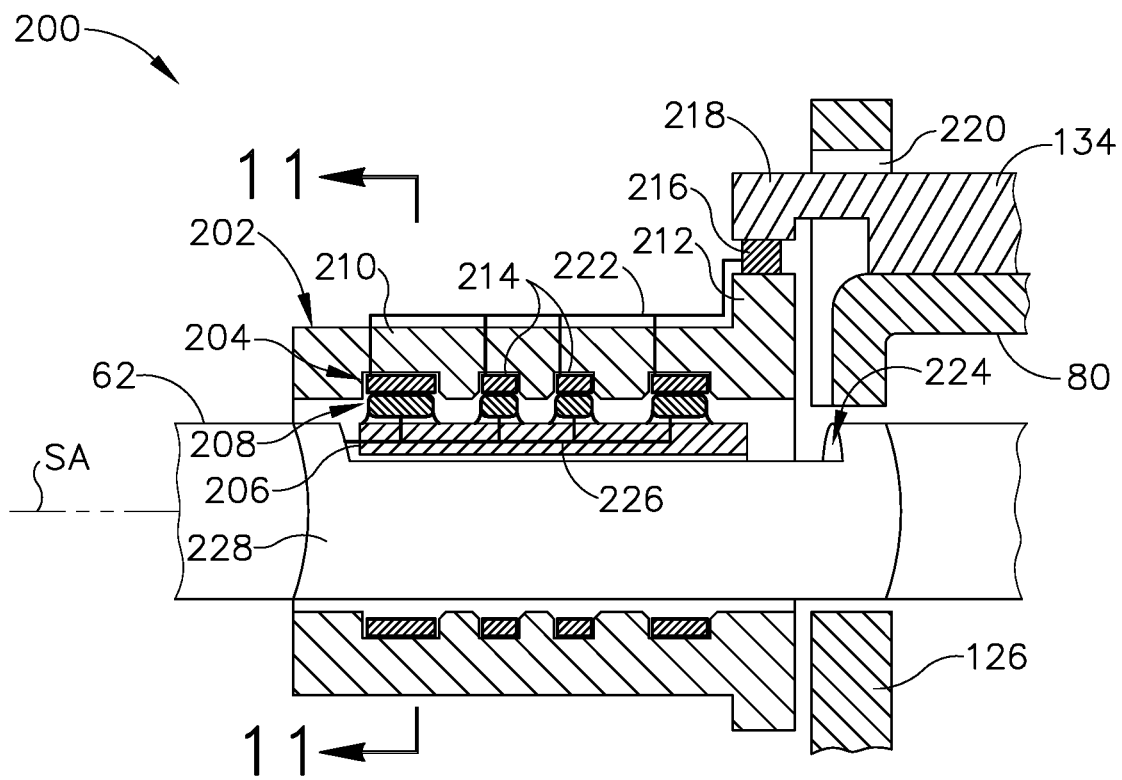
FIG. 10 depicts a partial side cross-sectional view of the slip ring assembly and adjacent components of the shaft assembly of FIG. 9.
Figure 11:
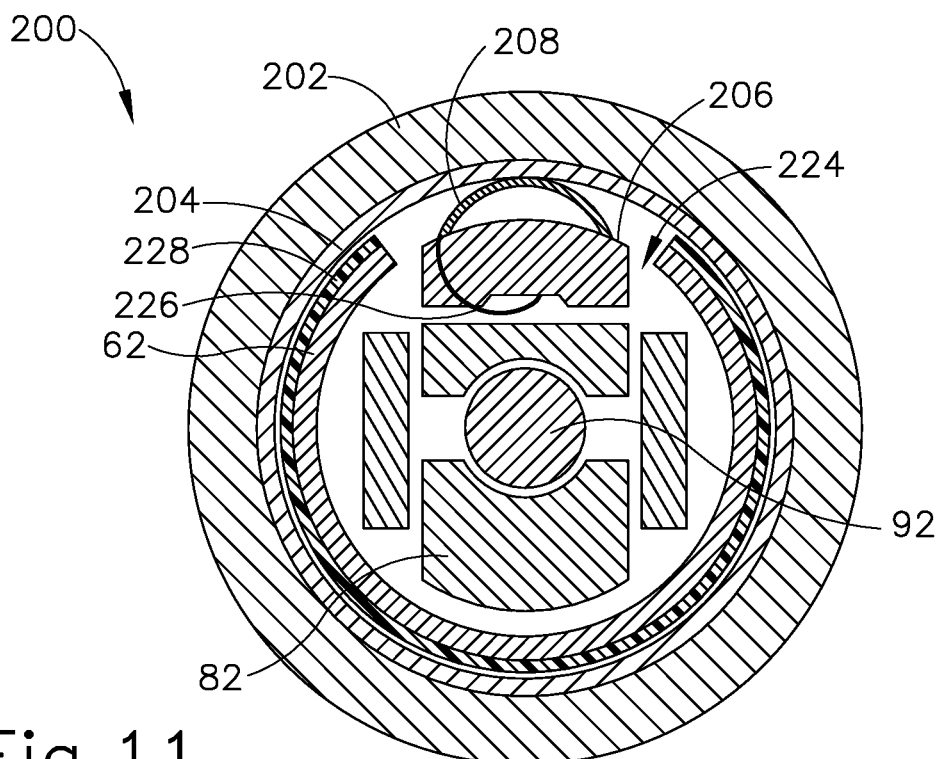
FIG. 11 depicts an end cross-sectional view of the slip ring assembly and adjacent components of the shaft assembly of FIG. 10, taken along line 11-11 of FIG. 10.

As shown in FIGS. 9-11, slip ring assembly (200) of the present example extends distally from chassis flange (126) of tool chassis (80) and is housed within nozzle (60). Slip ring assembly (200) includes an outer contact support structure in the form of a contact sleeve (202) that encircles a proximal portion of closure tube (62) and supports an axially-spaced arrangement of outer electrical contacts in the form of ring contacts (204). Slip ring assembly (200) further includes an inner contact support structure in the form of a contact block (206) that is coupled to the proximal portion of closure tube (62) and supports an axially-spaced arrangement of inner electrical contacts in the form of brush contacts (208). Each brush contact (208) is configured to electrically couple with a respective ring contact (204). As described in greater detail below, contact sleeve (202) and rings contacts (204) are configured to remain axially and rotationally fixed relative to tool chassis (80), while contact block (206) and brush contacts (208) are configured to rotate with closure tube (62) about shaft axis (SA) relative to contact sleeve (202) and other stationary components of surgical instrument (10). In other versions of slip ring assembly (200), a reverse configuration may be provided in which ring contacts (204) are supported by closure tube (62) and brush contacts (208) are supported by a stationary contact support structure positioned radially outward of closure tube (62), such that ring contacts (204) are configured to rotate relative to brush contacts (208).

As shown best in FIG. 10, contact sleeve (202) includes a cylindrical body (210) that encircles closure tube (62) coaxially, and a proximal flange (212) that confronts distal chassis flange (126) of tool chassis (80). Each ring contact (204) is recessed within a respective groove (214) formed in a radially inner surface of cylindrical body (210), such that ring contacts (204) face inwardly toward and are spaced radially outwardly from an outer surface of closure tube (62). Ring contacts (204) may be formed through stamping, rolling, and welding of sheet material, or through laser-cutting of tube stock material, for example. Contact sleeve (202) may be formed of an electrically insulative material, such as plastic, that electrically insulates ring contacts (204) from one another. As described in greater detail below, each ring contact (204) is spaced axially from the one or more immediately adjacent ring contacts (204), and each respective brush contact (208) is likewise spaced axially from the one of more immediately adjacent brush contacts (208), by an axial distance suitable to provide a minimum impedance that prevents electrical shorting between axially adjacent contacts (204, 208) in the presence of fluid.

Proximal flange (212) of contact sleeve (202) includes an electrical connector (216) that is configured to couple with a distal electrical connector portion (218) of shaft circuit board (134), which projects distally through an opening (220) formed in chassis flange (126). Electrical connector (216) is electrically coupled with ring contacts (204) via outer leads (222). Electrical connectors (216, 218) are configured to releasably couple together, for example via snap-fit engagement, to define an in-line slip connection that enables selective assembly and disassembly of slip ring assembly (200) along shaft axis (SA), for example for cleaning purposes. Electrical connectors (216, 218) thus cooperate to electrically couple slip ring assembly (200) with shaft circuit board (134). Shaft circuit board (134), in turn, is electrically coupled with the electrical components of handle assembly (12), including handle circuit board (46), via engagement of shaft electrical connector (152) with handle electrical connector (156) in the manner described above. It will be understood that shaft and handle electrical connectors (152, 156) may be substituted with alternative electrical connectors of the exemplary types disclosed in the references incorporated by reference herein.

Figure 12:
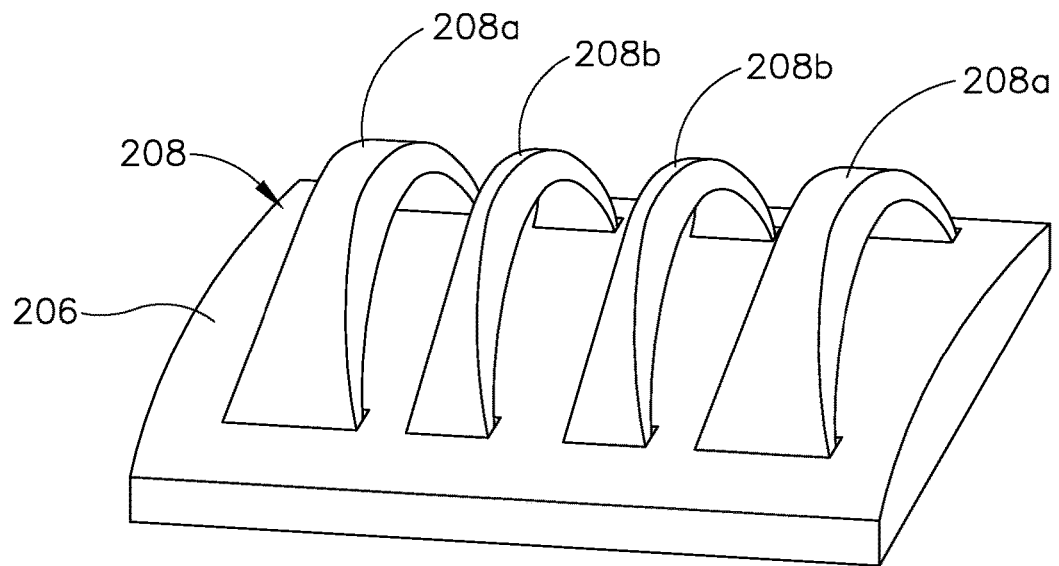
FIG. 12 depicts a perspective view of a contact block with brush contacts of the slip ring assembly of FIG. 9.

As shown in FIGS. 10-12, contact block (206) of the present example has a generally rectangular body and is exposed through a longitudinally extending opening (224) formed in the upper side of the proximal portion of closure tube (62). Similar to contact sleeve (202), contact block (206) may be formed of an electrically insulating material that electrically insulates brush contacts (208) from one another. Contact block (206) is supported by closure tube (62) such that contact block (206) is configured to rotate with closure tube (62) about shaft axis (SA). In the present example, contact block (206) is also longitudinally slidable relative to closure tube (62). This enables closure tube (62) to translate proximally and distally relative to contact block (206), to thereby actuate anvil (74) of end effector (16) between open and closed positions in the manner described above, while contact block (206) remains axially fixed relative to contact sleeve (202). This configuration, enabled by a suitable length of longitudinal opening (224), allows brush contacts (208) to remain axially aligned with, and thereby electrically coupled to, the respective ring contacts (204) even during actuation of closure tube (62). In other examples, contact block (206) may be fixed axially to closure tube (62) and thus configured to translate with closure tube (62) relative to tool chassis (80). In such examples, contact sleeve (202) may be configured to translate axially with closure tube (62) and contact block (206) relative to tool chassis (80), to maintain axial alignment of joined electrical contacts (204, 208), while remaining rotationally fixed relative to tool chassis (80).

Figure 13A:
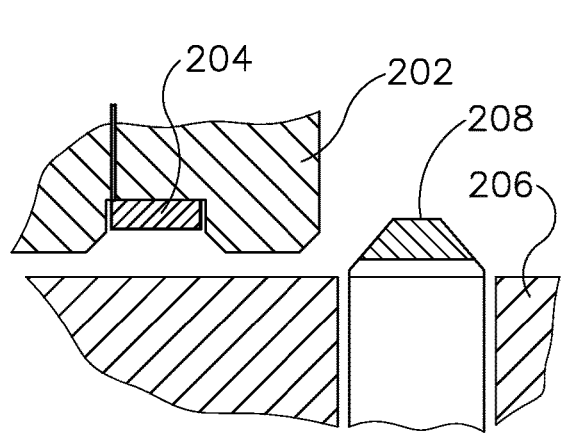
FIG. 13A depicts a side cross-sectional view of the contact block and a contact sleeve of the slip ring assembly of FIG. 9, showing the contact block and the contact sleeve in a pre-assembled state.
Figure 13B:
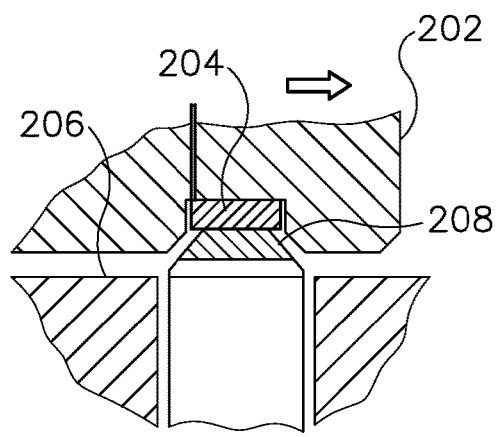
FIG. 13B depicts a side cross-sectional view of the contact block and the contact sleeve of FIG. 13A, showing the contact block and the contact sleeve in an assembled state.

As shown best in FIG. 12, brush contacts (208) of the present example are in the form of arched spring contacts that project radially outwardly from contact block (206). As shown in FIG. 10, brush contacts (208) are electrically coupled with one or more sensors or other electrical devices, such as electrodes, supported by shaft assembly (14) via inner leads (226) that extend through contact block (206). As shown in FIGS. 12-13B, each brush contact (208) includes chamfered proximal and distal edges configured to facilitate sliding engagement of contact sleeve (202) over brush contacts (208) during assembly of contact sleeve (202) with shaft assembly (14), or during subsequent disassembly. Contact sleeve (202) may be slid proximally over closure tube (62) and brush contacts (208), as shown in FIGS. 13A-13B, until sleeve electrical connector (216) engages distal electrical connector portion (218) of shaft circuit board (134), as shown in FIG. 10.

As shown best in FIGS. 10 and 11, slip ring assembly (200) further includes a layer (228) of electrically insulative material that encircles the outer surface of the proximal portion of closure tube (62) that supports contact block (206). In the present example, insulative layer (228) extends longitudinally such that a proximal end of layer (228) is positioned proximally of a proximal end of opening (224) and a proximal-most ring contact (204), and a distal end of layer is positioned distally of a distal end of opening (224) and a distal-most ring contact (204). Insulative layer (228) is configured to prevent electrical shorting of electrical contacts (204, 208) through closure tube (62) in the presence of fluid in slip ring assembly (200). In some versions, insulative layer (228) may extend longitudinally along closure tube (62) for lengths greater than the exemplary length shown and described herein.

Figure 14:
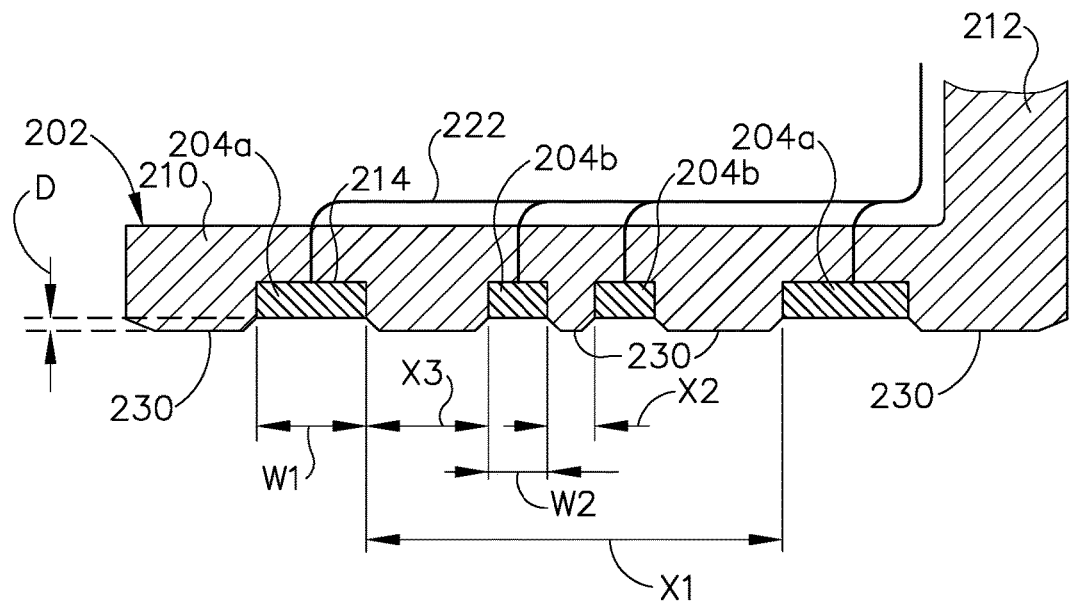
FIG. 14 depicts a side cross-sectional view of a portion of the contact sleeve of the slip ring assembly of FIG. 9.

As shown best in FIGS. 12 and 14, ring contacts (204) of contact sleeve (202) include a pair of high-power (or "high-energy") ring contacts (204a), and a pair of low-power (or "low-energy") ring contacts (204b). Similarly, brush contacts (208) include a corresponding pair of high-power brush contacts (208a) that couple with high-power ring contacts (204a), and a pair of low-power brush contacts (208b) that couple with low-power ring contacts (204b). High-power contacts (204a, 208a) correspond to electrical pathways configured to transmit comparatively higher levels of electrical energy, such as RF energy suitable to treat tissue in an electrosurgical procedure. Low-power ring contacts (204b) correspond to electrical pathways configured to transmit comparatively lower levels of electrical energy, such as electrical signals generated by one or more sensors of shaft assembly (14). Accordingly, in the present example high-power contacts (204a, 208a) are formed with a greater axial width than low-power contacts (204b, 208b). In particular, as shown in FIG. 14, high-power ring contacts (204a) have a greater axial width (W1), and low-power ring contacts (204b) have a smaller axial width (W2).

In one example, a first coupled pair of high-power contacts (204a, 208a) correspond to a high-power active path, and the second coupled pair of high-power contacts (204a, 208a) correspond to a high-power return path. Similarly, a first coupled pair of low-power contacts (204b, 208b) correspond to a low-power active path, and the second coupled pair of low-power contacts (204b, 208b) correspond to a low-power return path. While the exemplary version of slip ring assembly (200) shown and described herein includes four ring contacts (204) and four brush contacts (208), various other suitable quantities of contacts (204, 208) may be provided in other versions to accommodate various quantities of electrical pathways.

As noted above, each ring contact (204) and each brush contact (208) is spaced axially from the other ring contacts (204) and the other brush contacts (208), respectively, by an axial distance suitable to achieve a minimum impedance that prevents electrical shorting among ring contacts (204) and among brush contacts (208) in the presence of fluid. In particular, each high-power source contact (204a, 208a) is spaced axially from the respective high-power return contact (204a, 208a) by an axial distance suitable to prevent electrical shorting therebetween in the presence of fluid. Similarly, each low-power source contact (204b, 208b) is spaced axially from the respective low-power return contact (204b, 208b) by an axial distance suitable to prevent electrical shorting therebetween in the presence of fluid. Additionally, each individual ring contact (204) is spaced axially from the one or more immediately adjacent ring contacts (204) by an axial distance suitable to prevent electrical shorting therebetween in the presence of fluid. Likewise, each individual brush contact (208) is spaced axially from the one or more immediately adjacent ring contacts (204) by an axial distance suitable to prevent electrical shorting therebetween in the presence of fluid.

FIG. 14 shows an exemplary arrangement of ring contacts (204) in which high-power ring contacts (204a) are disposed at proximal and distal positions along the length of contact sleeve (202), and low-power ring contacts (204b) are disposed at medial positions between high-power contacts (204a). Brush contacts (208) of the present example are arranged in a similar manner on contact block (206). Each ring contact (204) is recessed within its respective groove (214) of contact sleeve (202) such that the exposed surface of ring contact (204) is disposed at a radial depth (D) from the radially inner surface of contact sleeve (202). High-power contacts (204a) are spaced apart axially by a first axial distance (X1), and low-power contacts (204b) are spaced apart axially by a second axial distance (X2) that is less than first axial distance (X1). Additionally, each low-power contact (204b) is spaced axially from the immediately adjacent high-power contact (204a) by a third axial distance (X3), which may be greater than second axial distance (X2) but less than first axial distance (X1), such that the axial spacing between adjacent ring contacts (204) is non-uniform. Accordingly, axial distances (X1, X2, X3) of the present example are characterized as follows: X1>X3>X2. Additionally, first axial distance (X1) may be characterized as follows: X1=X2+2(X3)+2(W2). It will be appreciated that brush contacts (208) may be provided with axial widths and axial spacings similar to those of ring contacts (204), such that brush contacts (208) properly align with respective ring contacts (204).

In one example, each high-power ring contact (204a) may have an axial width (W1) of approximately 0.100 inches, and each low-power ring contact (204b) may have an axial width (W2) of approximately 0.050 inches. Additionally, low-power ring contacts (204b) may be spaced apart by a second axial distance (X2) of approximately 0.050 inches, and each low-power ring contact (204b) may be spaced axially from the immediately adjacent high-power ring contact (204a) by a third axial distance (X3) of approximately 0.100 inches.

Figure 15:
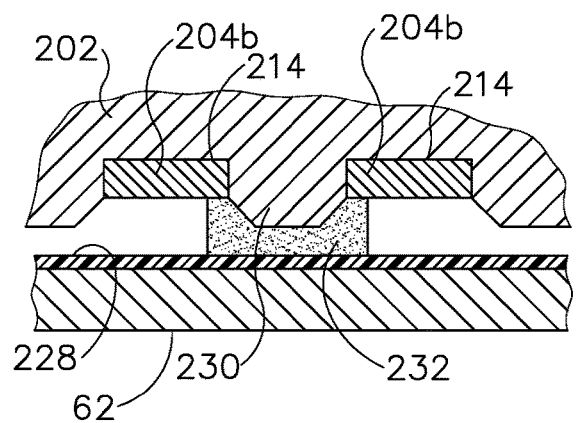
FIG. 15 depicts an enlarged side cross-sectional view of the contact sleeve of the slip ring assembly and a closure tube of the shaft assembly of FIG. 9, showing a fluid bridge formed between adjacent electrical contacts of the contact sleeve.

FIG. 15 shows an enlarged view of low-power ring contacts (204b) of contact sleeve (202). As discussed above, each ring contact (204) of the present example is recessed within a respective groove (214) formed in the radially inner surface of contact sleeve (202). Accordingly, each ring contact (204) is separated from each adjacent ring contact (204) by an annular rim (230) defined by contact sleeve body (210). Annular rim (230) functions as an electrically insulating barrier in the presence of a fluid bridge (232) that may form between axially adjacent contacts (204, 208) during use. Axial distances (X2, X3) between adjacent ring contacts (204) may be selected such that each electrically insulating rim (230) promotes an electrical impedance within the respective fluid bridge (232) that is sufficient to prevent electrical shorting through fluid bridge (232). Additionally, each rim (230) may have chamfered proximal and distal edges configured to engage brush contacts (208) to facilitate sliding of contact sleeve (202) over brush contacts (208) during assembly and disassembly of slip ring assembly (200), as described above in connection with FIGS. 12-13B.

Figure 16:
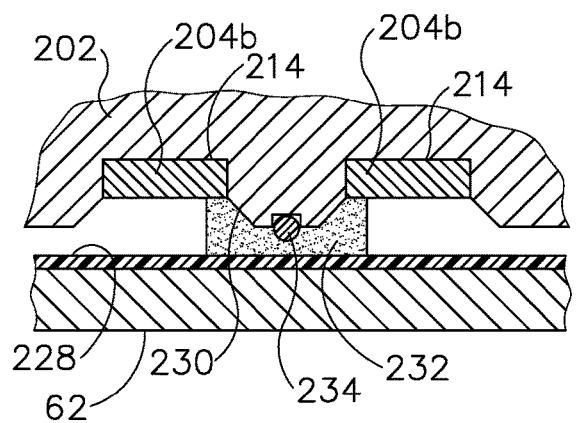
FIG. 16 depicts an enlarged side cross-sectional view of the contact sleeve and the closure tube of FIG. 15, showing an electrically insulating element positioned between adjacent electrical contacts of the contact sleeve.

FIG. 16 shows an exemplary alternative configuration in which the electrically insulating effect of rim (230) between low-power ring contacts (204b) is enhanced by an electrically insulating element (234), secured to rim (230). Electrically insulating element (234), which may be in the form of an O-ring for example, projects radially from rim (230) in a direction toward closure tube (62), and is configured to increase the impedance in the respective fluid bridge (232). In some cases, inclusion of an electrically insulating element (234) between two ring contacts (204) may enable the corresponding axial spacing therebetween (X2, X3) (i.e., the axial width of the respective rim (230)) to be reduced while still effectively preventing electrical shorts between the adjacent ring contacts (204) through fluid bridge (232). Accordingly, it will be understood in light the description provided above that axial spacings (X1, X2, X3) between contacts (204, 208), electrical contact axial widths (W1, W2), ring contact recess depth (D), and the presence of electrically insulating barriers between axially adjacent contacts (204, 208) collectively affect the resulting impedance of a fluid bridge (232) formed between adjacent contacts (204, 208). Accordingly, any one or more of these factors may be suitably adjusted as desired to achieve a certain minimum impedance sufficient to prevent electrical shorting in slip ring assembly (200) in the presence of fluid. In some examples, electrical shorting of electrical contacts (204, 208) through fluid may be further averted by coating one of more contacts (204, 208) with a conductive composite material, such as carbon ink, silver-doped epoxy, or nickel-doped epoxy, for example.

III. Exemplary Electrical Connectors in End Effector

Figure 17:
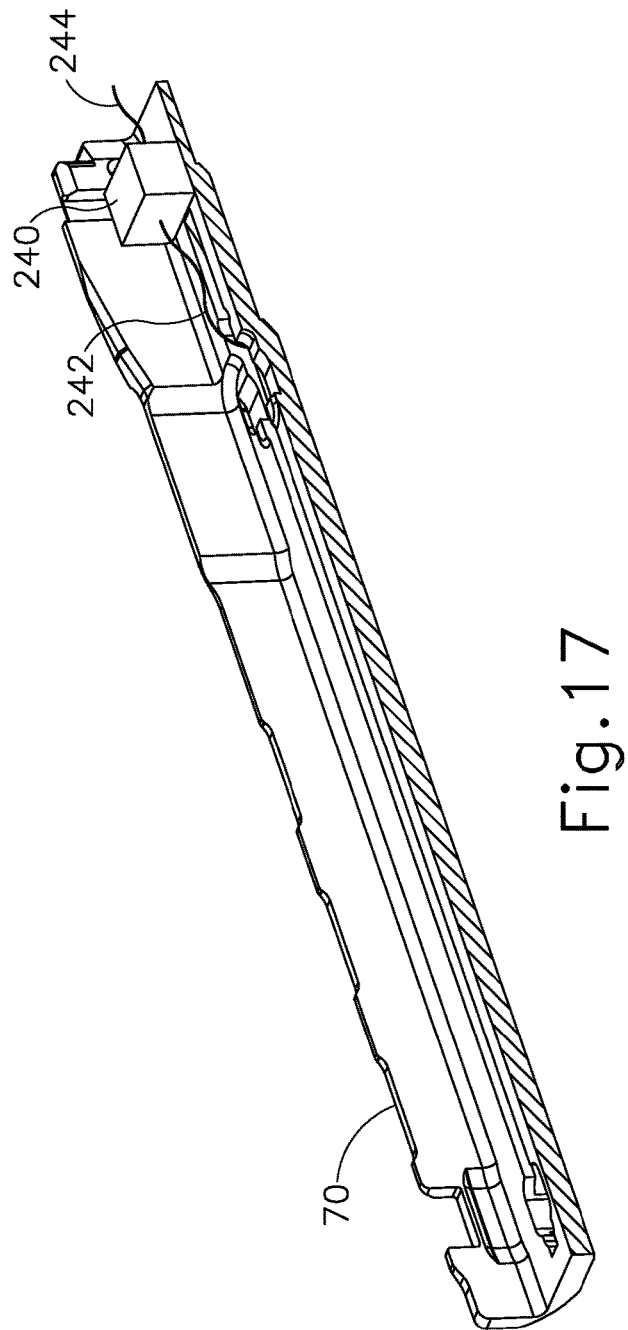
FIG. 17 depicts a cutaway perspective view of a channel of the end effector of FIG. 6, schematically showing an electrical connector coupled to the channel.

It may be desirable to provide a distal portion of shaft assembly (14) with an electrical connector to facilitate electrical coupling of one or more sensors or other electrical elements of shaft assembly (14) with a slip ring assembly of surgical instrument (10), such as one of slip ring assemblies (120, 200). FIG. 17 shows an exemplary arrangement in which a proximal end of end effector channel (70) supports an electrical connector (240), depicted schematically. Electrical connector (240) is configured to electrically couple sensors or other electrical elements of shaft assembly (14) with the rotating electrical contacts of the slip ring assembly of instrument (10). For instance, electrical connector (240) may be configured to electrically couple such sensors and/or other electrical elements with the electrical contacts of distal flange (124) of slip ring assembly (120), or with brush contacts (208) of slip ring assembly (200). As shown schematically in FIG. 17, electrical connector (240) accomplishes this by electrically coupling a first plurality of conductive members (242) with a second plurality of conductive members (244), each of which may be in the form of wires. First conductive members (242) extend distally and electrically communicate with the sensors and/or other electrical elements of shaft assembly (14). Second conductive members (244) extend proximally and electrically communicate with the rotating electrical contacts of the slip ring assembly. FIGS. 18-20C, described below, show various exemplary configurations of electrical connector (240).

Figure 18:
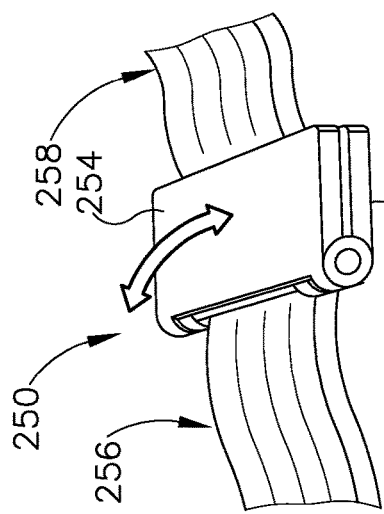
FIG. 18 depicts a perspective view of a first exemplary configuration of the electrical connector of FIG. 17.

FIG. 18 shows an electrical connector (250) that embodies a first exemplary configuration of electrical connector (240). Electrical connector (250) is in the form of a hinged zero-insertion-force ("ZIF") connector having a base plate (252) and a locking lever (254) pivotably coupled to base plate (252). A first set of wires (256) is electrically coupled with base plate (252) and extends distally to electrically connect with the sensors or other electrical elements of end effector (16), for example via electrical traces (182) described above. A second set of wires (258) is configured to be received proximally by electrical connector (250) for electrical coupling with first wires (256). Locking lever (254) is configured to pivot relative to base plate (252) between an open position in which connector (250) is configured to receive second wires (258), and a closed position in which locking lever (254) is configured to clamp second wires (258) against base plate (252) and thereby electrically couple first wires (256) with second wires (258). Electrical connector (250) may be oriented within end effector (16) such that base plate (252) is secured to channel (70), and such that locking lever (254) is configured to pivot about an axis that extends transversely to shaft axis (SA).

Figure 19:
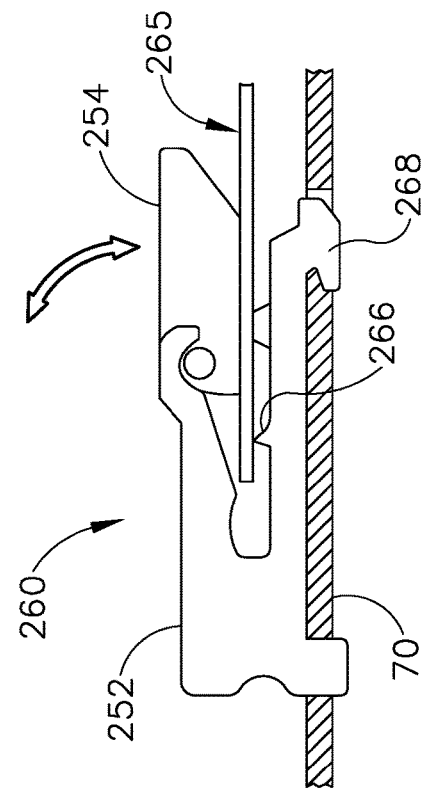
FIG. 19 depicts a side sectional view of another exemplary configuration of the electrical connector of FIG. 17.

FIG. 19 shows another electrical connector (260) that embodies a second exemplary configuration of electrical connector (240). Similar to electrical connector (250), electrical connector (260) is in the form of a hinged zero-insertion-force ("ZIF") connector having a base plate (262) and a locking lever (264) pivotably coupled to base plate (262). Base plate (262) is configured to electrically couple with a first set of wires (not shown) coupled with sensors or other electrical elements of end effector (16). Locking lever (264) is configured to pivot between open and closed positions relative to base plate (262) to clamp a second set of wires (265) against base plate (262), via a spike (266), and thereby electrically couple the first wires with second wires (265). Connector (260) of the present example is configured to lockingly engage channel (70) of end effector (16), for example with a snap-fit engagement. Base plate (262) includes a lower arm (268) configured to project downwardly through an opening formed in a base surface of channel (70), and hook the base surface against base plate (262).

Figure 20A:
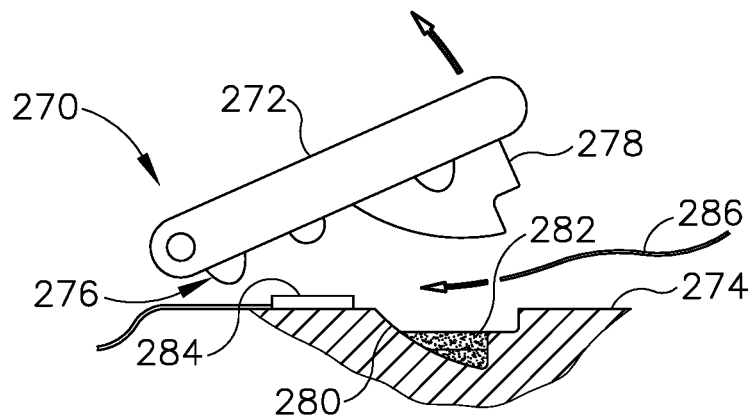
FIG. 20A depicts a side cross-sectional view of another exemplary configuration of the electrical connector of FIG. 17, showing the electrical connector in an open state.
Figure 20B:
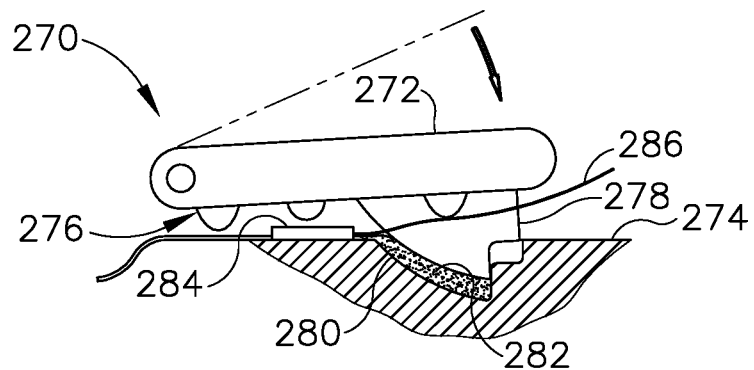
FIG. 20B depicts a side cross-sectional view of the electrical connector of FIG. 20A, showing the electrical connector in a partially closed state.
Figure 20C:
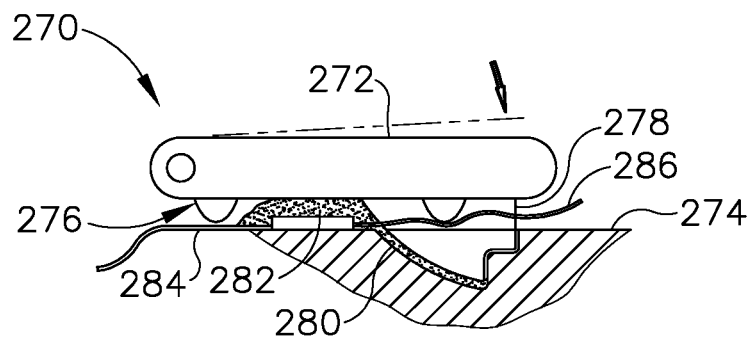
FIG. 20C depicts a side cross-sectional view of the electrical connector of FIG. 20B, showing the electrical connector in a fully closed state.

FIGS. 20A-20C show another electrical connector (270) that embodies a third exemplary configuration of electrical connector (240). Electrical connector (270) includes a lever (272) pivotably coupled to a base structure (274) that is supported by end effector channel (70), or otherwise defined by channel (70). The underside of lever (272) includes a plurality of teeth (276) arranged along a length of lever (272), and a fin (278) arranged at a free end of lever (272). Fin (278) is configured to seat within a recess (280) formed in base structure (274) when lever (272) is pivoted from an open position (FIG. 20A) to a closed position (FIG. 20C). Recess (280) is at least partially filled with a multi-part epoxy (282).

As shown in FIG. 20A, with lever (272) in the open position, a first wire (284) is inserted underneath lever (272) from a first direction, and a second wire (286) is inserted underneath lever (272) from an opposed second direction, such that exposed ends of wires (284, 286) overlap one another. As shown in FIG. 20B, lever (272) is pivoted downwardly toward base structure (274) so that fin (278) is received within recess (280) and causes the multiple parts of epoxy (282) to mix together and begin curing. As shown in FIG. 20C, as fin (278) fully seats within recess (280), fin (278) causes mixed epoxy (282) to travel upwardly from recess (280) and encapsulate the overlapping wires (284, 286). Upon curing, epoxy (282) bonds wires (284, 286) together and thereby establishes a permanent electrical connection. Lever (272) may be held in its fully closed position while epoxy (282) cures by any suitable locking mechanism, such as a snap feature for example.

Multi-part, mixable epoxy may also be used in connection with either of connectors (250, 260) described above, as well as various other configurations of electrical connector (240). For instance, connector (250, 260) may include an epoxy capsule that is configured to be ruptured by locking lever (254, 264) when lever (254, 264) is pivoted from its open position to its closed position. Epoxy would then cure while lever (254, 264) remains in its closed position, thereby strengthening the electrical connector established by connector (260). In other examples, any configuration of electrical connector (240), including those described above, may be coated with a suitable thermoplastic, such as TECH-NOMELT®, in whole or in part to prevent unintended disengagement of wires from electrical connector (240) after assembly.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body assembly; (b) a shaft assembly extending distally from the body assembly along a shaft axis, wherein the shaft assembly includes an outer tube configured to rotate relative to the body assembly about the shaft axis; (c) an end effector at a distal end of the shaft assembly, wherein the end effector is operable to treat tissue; and (d) a slip ring assembly configured to enable electrical communication between the shaft assembly and the body assembly while permitting relative rotation therebetween, wherein the slip ring assembly comprises: (i) a first electrical contact supported by the outer tube, and (ii) a second electrical contact positioned radially outward of the outer tube, wherein the first and second electrical contacts are electrically coupled together, wherein the first electrical contact is configured to rotate with the outer tube about the shaft axis relative to the second electrical contact while the first and second electrical contacts remain electrically coupled.

Example 2

The surgical instrument of Example 1, wherein the slip ring assembly is disposed at a proximal end of the shaft assembly.

Example 3

The surgical instrument of any of the preceding Examples, wherein the shaft assembly further comprises a nozzle, wherein the slip ring assembly is housed within the nozzle.

Example 4

The surgical instrument of any of the preceding Examples, wherein the slip ring assembly further comprises a contact support structure that supports the second electrical contact, wherein the contact support structure is rotationally fixed relative to the body assembly.

Example 5

The surgical instrument of Example 4, wherein the shaft assembly includes a chassis that rotatably supports the outer tube, wherein the contact support structure is coupled to the chassis.

Example 6

The surgical instrument of Example 5, wherein the contact support structure extends distally from the chassis.

Example 7

The surgical instrument of any of Examples 4 through 6, wherein the contact support structure comprises a sleeve, wherein the sleeve encircles the outer tube and the first electrical contact.

Example 8

The surgical instrument of any of the preceding Examples, wherein one of the first electrical contact or the second electrical contact comprises a ring contact, wherein the other of the first electrical contact or the second electrical contact comprises a brush contact.

Example 9

The surgical instrument of Example 8, wherein the brush contact includes an angled distal edge, wherein the angled distal edge is configured to promote sliding engagement of the first contact with the second contact in a direction parallel to the shaft axis.

Example 10

The surgical instrument of any of the preceding Examples, wherein the slip ring assembly includes a plurality of first electrical contacts spaced axially and supported by the outer tube, and a plurality of second electrical contacts spaced axially and positioned radially outward of the first electrical contacts, wherein the first electrical contacts are configured to rotate with the outer tube relative to the second electrical contacts while remaining electrically coupled with the second electrical contacts.

Example 11

The surgical instrument of Example 10, wherein the first electrical contacts are spaced apart with non-uniform axial spacing, wherein the second electrical contacts are spaced apart with non-uniform axial spacing.

Example 12

The surgical instrument of Example 10, wherein the slip ring assembly further comprises a contact support structure that supports the second electrical contacts, wherein each adjacent pair of the second electrical contacts is separated by an electrically insulating barrier.

Example 13

The surgical instrument of Example 12, wherein the electrically insulating barrier is defined by the contact support structure.

Example 14

The surgical instrument of any of Examples 12 through 13, wherein the electrically insulating barrier comprises an electrically insulating element coupled to the contact support structure.

Example 15

The surgical instrument of any of the preceding Examples, wherein the shaft assembly is configured to releasably attach to the body assembly, wherein the body assembly includes a first electrical connector, wherein the shaft assembly includes a second electrical connector configured to electrically couple with the first electrical connector when the shaft assembly is attached to the body assembly.

Example 16

A surgical instrument, comprising: (a) a body assembly; (b) a shaft assembly extending distally from the body assembly along a shaft axis, wherein the shaft assembly includes an outer tube configured to rotate relative to the body assembly about the shaft axis; (c) an end effector at a distal end of the shaft assembly, wherein the end effector is operable to treat tissue; and (d) a slip ring assembly configured to enable electrical communication between the shaft assembly and the body assembly while permitting relative rotation therebetween, wherein the slip ring assembly comprises: (i) a plurality of brush contacts spaced axially along the shaft axis, and (ii) a plurality of ring contacts spaced axially along the shaft axis, wherein the ring contacts encircle and electrically couple with the brush contacts, wherein one of the brush contacts or the ring contacts are configured to rotate with the outer tube about the shaft axis relative to the other of the brush contacts or the ring contacts while the brush contacts and the ring contacts remain electrically coupled.

Example 17

The surgical instrument of Example 16, wherein the brush contacts and the ring contacts are configured to electrically engage at a location radially outward of the outer tube.

Example 18

The surgical instrument of any of Examples 16 through 17, wherein the brush contacts are supported by the outer tube, wherein the ring contacts are supported by a sleeve that encircles the outer tube.

Example 19

A surgical instrument, comprising: (a) a body assembly; (b) a shaft assembly extending distally from the body assembly along a shaft axis, wherein the shaft assembly includes an outer tube configured to rotate relative to the body assembly about the shaft axis; (c) an end effector at a distal end of the shaft assembly, wherein the end effector is operable to treat tissue; and (d) a slip ring assembly configured to enable electrical communication between the shaft assembly and the body assembly while permitting relative rotation therebetween, wherein the slip ring assembly comprises: (i) a plurality of brush contacts arranged axially, wherein the brush contacts are spaced apart with non-uniform axial spacing, and (ii) a plurality of ring contacts arranged axially and configured to electrically couple with the brush contacts, wherein the ring contacts are spaced apart with non-uniform axial spacing, wherein the non-uniform axial spacing of the contacts is configured to establish impedances that prevent electrical shorting between non-coupled pairs of the contacts in the presence of fluid, wherein one of the brush contacts or the ring contacts are configured to rotate with the outer tube about the shaft axis relative to the other of the brush contacts or the ring contacts while the brush contacts and the ring contacts remain electrically coupled.

Example 20

The surgical instrument of Example 19, wherein the ring contacts include a pair of high-power ring contacts each having a first axial width and a pair of low-power ring contacts each having a second axial width smaller than the first axial width, wherein the high-power ring contacts are spaced apart by a first axial distance and the low-power ring contacts are spaced apart by a second axial distance smaller than the first axial distance.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/934,139, entitled "Surgical Instrument With Compressible Electrical Connector," filed on Mar. 23, 2018, published as U.S. Pub. No. 2019/0290307 on Sep. 26, 2019, issued as U.S. Pat. No. 10,842,517 on Nov. 24, 2020; U.S. application Ser. No. 15/934,148, entitled "Seal for Surgical Instrument," filed on Mar. 23, 2018, published as U.S. Pub. No. 2019/0290308 on Sep. 26, 2019, issued as U.S. Pat. No. 10,799,257 on Oct. 13, 2020; U.S. application Ser. No. 15/934,160, entitled "Surgical Instrument with Recessed Contacts and Electrically Insulting Barriers," filed on Mar. 23, 2018, published as U.S. Pub. No. 2019/0290269 on Sep. 26, 2019, issued as U.S. Pat. No. 11,026,681 on June 8, 2021; U.S. application Ser. No. 15/934,166, entitled "Surgical Instrument with Electrical Contact Under Membrane," filed on Mar. 23, 2018, published as U.S. Pub. No. 2019/0290270 on Sep. 26, 2019, issued as U.S. Pat. No. 10,631,860 on Apr. 28, 2020; U.S. application Ser. No. 15/934,173, entitled "Staple Cartridge with Short Circuit Prevention Features," filed on Mar. 23, 2018, published as U.S. Pub. No. 2019/0290271 on Sep. 26, 2019, issued as U.S. Pat. No. 10,639,038 on May 5, 2020; and U.S. application Ser. No. 15/934,180, entitled "Surgical Instrument with Capacitive Electrical Interface," filed on Mar. 23, 2018, published as U.S. Pub. No. 2019/0290272 on Sep. 26, 2019, issued as U.S. Pat. No. 10,779,828 on Sep. 22, 2020.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. Pub. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A slip ring assembly for a surgical instrument having a body and a shaft tube extending distally from and rotatable relative to the body, the slip ring assembly comprising:
   (a) an outer contact support structure;
   (b) an inner contact support structure rotatable relative to the outer contact support structure about an axis, wherein one of the inner contact support structure or the outer contact support structure is configured to be rotationally fixed relative to the body, wherein the other of the inner contact support structure or the outer contact support structure is configured to be rotationally fixed relative to the shaft tube to thereby rotate with the shaft tube relative to the body about the axis;
   (c) a plurality of first electrical contacts spaced apart axially and supported by the inner contact support structure; and
   (d) a plurality of second electrical contacts spaced apart axially and supported by the outer contact support structure, wherein the plurality of second electrical contacts is positioned radially outward of the plurality of first electrical contacts, wherein the first and second electrical contacts are rotatable relative to each other about the axis while remaining electrically coupled to each other for enabling electrical communication between the shaft tube and the body while permitting relative rotation therebetween.

2. The slip ring assembly of claim 1, wherein the outer contact support structure encircles the plurality of first electrical contacts.

3. The slip ring assembly of claim 1, wherein one of the plurality of first electrical contacts or the plurality of second electrical contacts comprises a plurality of ring contacts.

4. The slip ring assembly of claim 3, wherein the other of the plurality of first electrical contacts or the plurality of second electrical contacts comprises a plurality of brush contacts.

5. The slip ring assembly of claim 4, wherein each of the brush contacts includes an angled distal edge, wherein the angled distal edge is configured to promote sliding engagement of the first contacts with the second contacts in a direction parallel to the axis.

6. The slip ring assembly of claim 1, wherein the first electrical contacts are spaced apart with non-uniform axial spacing.

7. The slip ring assembly of claim 6, wherein the second electrical contacts are spaced apart with non-uniform axial spacing.

8. The slip ring assembly of claim 1, wherein each adjacent pair of the second electrical contacts is separated by an electrically insulating barrier.

9. The slip ring assembly of claim 8, wherein the electrically insulating barrier is defined by the outer contact support structure.

10. The slip ring assembly of claim 8, wherein the electrically insulating barrier comprises an electrically insulating element coupled to the outer contact support structure.

11. The slip ring assembly of claim 1, wherein one of the outer contact support structure or the inner contact support structure includes a contact sleeve.

12. The slip ring assembly of claim 1, wherein one of the outer contact support structure or the inner contact support structure includes a contact block.

13. The slip ring assembly of claim 1, wherein one of the first contacts or the second contacts include a pair of high-power contacts each having a first axial width and a pair of low-power contacts each having a second axial width smaller than the first axial width.

14. The slip ring assembly of claim 13, wherein the high-power contacts are spaced apart by a first axial distance and the low-power contacts are spaced apart by a second axial distance smaller than the first axial distance.

15. The slip ring assembly of claim 14, wherein each of the low-power contacts is spaced apart from an adjacent high-power contact of the pair of high-power contacts by a third axial distance greater than the second axial distance and smaller than the first axial distance.

16. A surgical instrument, comprising:
(a) a body assembly;
(b) a shaft assembly extending distally from the body assembly along a shaft axis, wherein the shaft assembly includes a shaft tube configured to rotate relative to the body assembly about the shaft axis;
(c) an end effector at a distal end of the shaft assembly, wherein the end effector is operable to treat tissue; and
(d) a slip ring assembly configured to enable electrical communication between the shaft assembly and the body assembly while permitting relative rotation therebetween, wherein the slip ring assembly comprises:
(i) a plurality of first contacts spaced apart axially along the shaft axis, and
(ii) a plurality of second contacts spaced apart axially along the shaft axis, wherein the second contacts encircle and electrically couple with the first contacts,
wherein one of the first contacts or the second contacts are configured to rotate with the shaft tube about the shaft axis relative to the other of the first contacts or the second contacts while the first contacts and the second contacts remain electrically coupled.

17. The surgical instrument of claim 16, wherein the first contacts and the second contacts are configured to electrically engage at a location radially outward of the shaft tube.

18. The surgical instrument of claim 16, wherein the first contacts are supported by the shaft tube, wherein the second contacts are supported by a sleeve that encircles the shaft tube.

19. A surgical instrument, comprising:
(a) a body assembly;
(b) a shaft assembly extending distally from the body assembly along a shaft axis, wherein the shaft assembly includes a shaft tube configured to rotate relative to the body assembly about the shaft axis;
(c) an end effector at a distal end of the shaft assembly, wherein the end effector is operable to treat tissue; and
(d) a slip ring assembly configured to enable electrical communication between the shaft assembly and the body assembly while permitting relative rotation therebetween, wherein the slip ring assembly comprises:
(i) a plurality of first contacts arranged axially, wherein the first contacts are spaced apart with non-uniform axial spacing, and
(ii) a plurality of second contacts arranged axially and configured to electrically couple with the first contacts,
wherein one of the first contacts or the second contacts are configured to rotate with the shaft tube about the shaft axis relative to the other of the first contacts or the second contacts while the first contacts and the second contacts remain electrically coupled.

20. The surgical instrument of claim 19, wherein the second contacts are spaced apart with non-uniform axial spacing, wherein the non-uniform axial spacing of the second contacts is configured to establish impedances that prevent electrical shorting between non-coupled pairs of the contacts in the presence of fluid.

* * * * *